United States Patent [19]

Martindale et al.

[11] Patent Number: 5,051,352
[45] Date of Patent: Sep. 24, 1991

[54] APPARATUS AND METHOD OF PRESERVING THE VIABILITY OF ANIMAL ORGANS

[75] Inventors: James G. Martindale, Costa Mesa; Ralph E. Purdy; George L. Stupecky, both of Irvine; Ronny G. Tidwell, Irvine, all of Calif.

[73] Assignee: The Regents of the University of California, Alameda, Calif.

[21] Appl. No.: 106,074

[22] Filed: Oct. 7, 1987

[51] Int. Cl.⁵ .............................. A01N 1/02
[52] U.S. Cl. .................... 435/1; 435/283; 435/284; 435/290; 435/291
[58] Field of Search .......... 435/1, 283, 284, 287, 435/290, 291, 240.2, 240.1; 604/118; 422/1; 137/540, 539, 535; 128/696, 697, 705, 733, 419 PT, 419 D, 897, 898; 600/21; 62/78

[56] References Cited

U.S. PATENT DOCUMENTS

| | | | |
|---|---|---|---|
| 3,843,455 | 10/1974 | Bier | 435/283 |
| 4,299,919 | 11/1981 | Jellinek | 435/283 |
| 4,403,988 | 9/1983 | Binard et al. | 604/118 |
| 4,513,752 | 4/1985 | Weyant | 128/696 |
| 4,666,425 | 5/1987 | Fleming | 435/283 |
| 4,781,686 | 11/1988 | Erickson | 604/118 |

FOREIGN PATENT DOCUMENTS 0200497  5/1983  German Democratic Rep. .................. 435/283
0814307  3/1981  U.S.S.R.

OTHER PUBLICATIONS

Noresson et al., Dialog Abstract; BIOSIS No. 75016370 (1982).

Primary Examiner—David L. Lacey
Assistant Examiner—William A. Beisner
Attorney, Agent, or Firm—Nilsson, Robbins, Dalgarn, Berliner, Carson & Wurst

[57] ABSTRACT

An apparatus and method of maintaining the viability of animal organs, and in particular human organs, by controlling the storage temperature of the organ and providing the organ with sufficient nutrients and oxygen, while also monitoring and maintaining the organ's transmembrane potential within a predefined range.

24 Claims, 4 Drawing Sheets

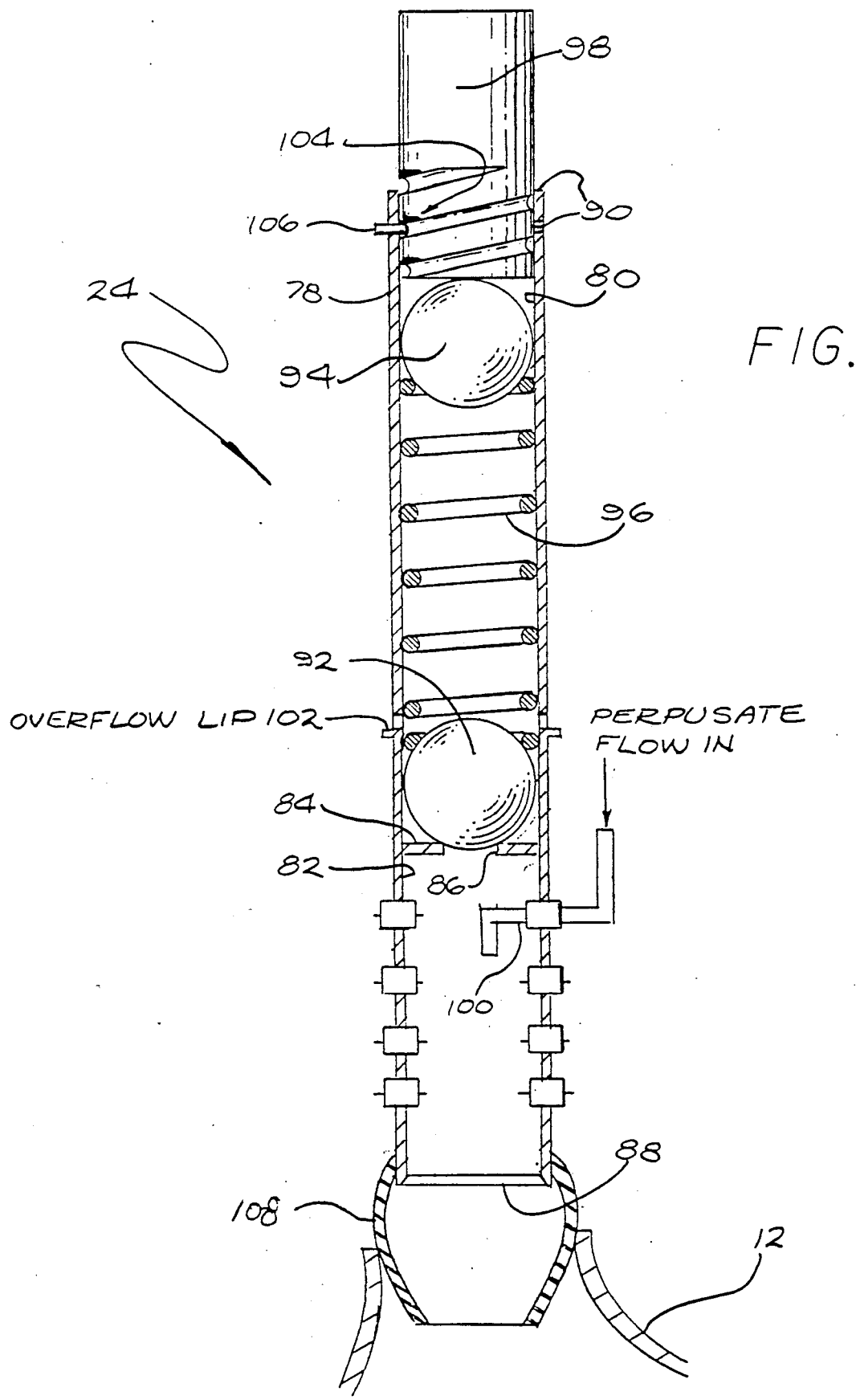

APPARATUS AND METHOD OF PRESERVING THE VIABILITY OF ANIMAL ORGANS

BACKGROUND OF THE INVENTION

The present invention is directed to the field of organ preservation, and in particular, to an apparatus and method of maintaining the viability of animal organs, tissue and various other animal parts.

There is a strong emphasis on maintaining the viability of animal organs, and in particular human organs, for long periods of time to increase the use of such organs for transplantation and medical research. Specifically, the ability to perform a transplant operation is dependent upon the availability of suitable organs. The availability of such organs is particularly dependent upon maintaining the viability of an organ after removal from its donor, and more so if the organ must be transported over a great distance to the intended recipient.

There is also a critical need to maintain the viability of organs for performing medical experiments on such organs. For example, it is safer to test new drugs on particular human organs than on humans themselves. However, in order to do such testing the organs, which have been removed from the donor body, must be maintained not only viable, but also in as close as possible to its natural state.

Presently available apparatus and methods take a number of different approaches to maintain the viability of animal organs for such uses. However, such apparatus are designed to minimize the normal metabolic functions of the organ. For example, presently available apparatus either completely freeze the organ, or lower the organ temperature to such a degree that there is a substantial suspension of the normal metabolic activities of the organ. In order to enhance the viability of the organ a nutrient solution, perfusate, is circulated through the organ.

Specific examples of these types of methods include maintaining the organ in a balanced electrolyte bath (hyperthermia), maintaining the organ at normal temperatures while storing the organ in an electrolyte bath under a positive pressure oxygen atmosphere (hypobaric) or pumping an oxygenated nutrient medium (a perfusate) through the organ to be preserved (perfusion). Apparatus which maintain an organ viability in accordance with one or more of these methods are disclosed in U.S. Pat. Nos. 3,406,531 (Swenson et al); 3,738,914 (Thorne et al); 3,545,221 (Swenson et al); 3,753,865 Belzer et al); 3,607,646 de Roissart); 3,772,153 (de Roissart) with the disclosure of all such references being incorporated herein by reference.

Thus, while presently available apparatus are suitable for maintaining the viability of organs, such apparatus can not maintain the normal metabolic activities of the organ. This limits the usefulness of such apparatus in drug research, since such research requires the ability to observe the effect that a drug will have upon the metabolic activities of the organ. The inability of presently available apparatus to maintain an organ in a state where the normal metabolic activities are allowed to continue has now been determined to be a function of numerous factors. In particular, it has now been determined that the temperature at which the organ is maintained as well as regulating the electrical potential of the organ is critical.

Previous apparatus have not attempted to regulate the electrical potential of the organs. It is well known that individual cells possess transmembrane potentials. That is, in each cell there is a distribution of electrical potential across the cell membrane. This potential exists because of the distribution of various types of ions on opposing sides of the cell membrane. That is, the distribution of one or more type of ions inside the cell membrane as opposed to the distribution of other types of ions outside the cell membrane causes an overall electrical potential or polarization of electrical charge along the cell membrane.

When this potential becomes sufficiently altered the cell is said to be excited. Specifically, when a resting cell is depolarized to a critical level, known as the threshold, the membrane becomes permeable and a regenerative inward current causes an action potential. The result is a variance in the cell membrane voltage which directly affects the activity of that cell.

The activity of various cells, as a function of the regulation of this transmembrane potential, will have a profound effect upon the organ in which the cells are located. That is, the metabolic activities of an organ is a function of the activity of individual cells. Thus, the regulation of the cellular transmembrane potential will directly affect the metabolic activity of the organ.

For example, the activity of muscle cells is affected by this transmembrane potential. Those organs which are characteristically dependent upon muscle cell activity, e.g., the heart, depend upon the regulation of this cellular transmembrane potential to control the muscular tissue activity. Nerve cells are another example of cells which are particularly affected by the regulation of this transmembrane potential. All organs depend to a varying extent upon the functioning of nerve cells and are thus susceptible to a depolarization of such cells.

This transmembrane potential can be affected by many conditions. For example, the concentration of various ions in a cell will affect the polarization of this membrane potential. Fluctuations in the cell physical environment will also have a profound effect upon the polarization of this transmembrane potential. In particular, temperature and electrical stimulation will affect this potential.

It can thus be seen that presently available apparatus are not suited for maintaining the viability of organs in a state whereby the organ maintains its normal metabolic activities. Furthermore, some presently available apparatus directly affect the transmembrane potential by freezing the organ. It would thus be beneficial to provide an apparatus which can store an organ in an environment as close as possible to its natural state. This includes not only maintaining such an organ providing the organ with sufficient nutrients and oxygen as previous apparatus have accomplished, but also by monitoring and regulating the temperature and transmembrane potential of the organ.

SUMMARY OF THE INVENTION

The present invention is directed to an apparatus and method of maintaining the viability of animal organs and in particular human organs, by providing the organ with sufficient nutrients and oxygen, while also controlling the storage temperature of the organ and monitoring and maintaining the organ's transmembrane potential.

Specifically, the instant invention is directed to an apparatus for maintaining the viability of animal organs. This apparatus includes a chamber in which the organ to be preserved is stored. A perfusate is circulated through both the organ and the chamber, which contains the nutrients suitable for the particular organ being stored in the chamber. The temperature of the perfusate is also monitored and maintained within a specific temperature range, while the perfusate is subjected to oxygenation to deliver sufficient oxygen to the organ being stored.

The apparatus also includes various devices for monitoring the electrophysical and electrochemical characteristics of the organ and the perfusate. The information derived from these monitoring devices allows for the calculation of the transmembrane potential of the organ. The apparatus includes suitable devices for generating and delivering electrical stimulation to the organ or which vary the ion concentration of the perfusate when the measured electrophysical and electrochemical characteristics vary from within predefined limits. These limits are those calculated for the organ while present in its natural resting state.

BRIEF DESCRIPTION OF THE DRAWINGS

The present invention may be better understood and its advantages will be apparent to those skilled in the art by reference to the accompanying drawings, wherein like reference numerals refer to like elements in the several Figures, and wherein:

FIG. 7 is a schematic illustration of a self-regulating valve in accordance with an embodiment of the invention.

DESCRIPTION OF THE INVENTION

Figure 1:
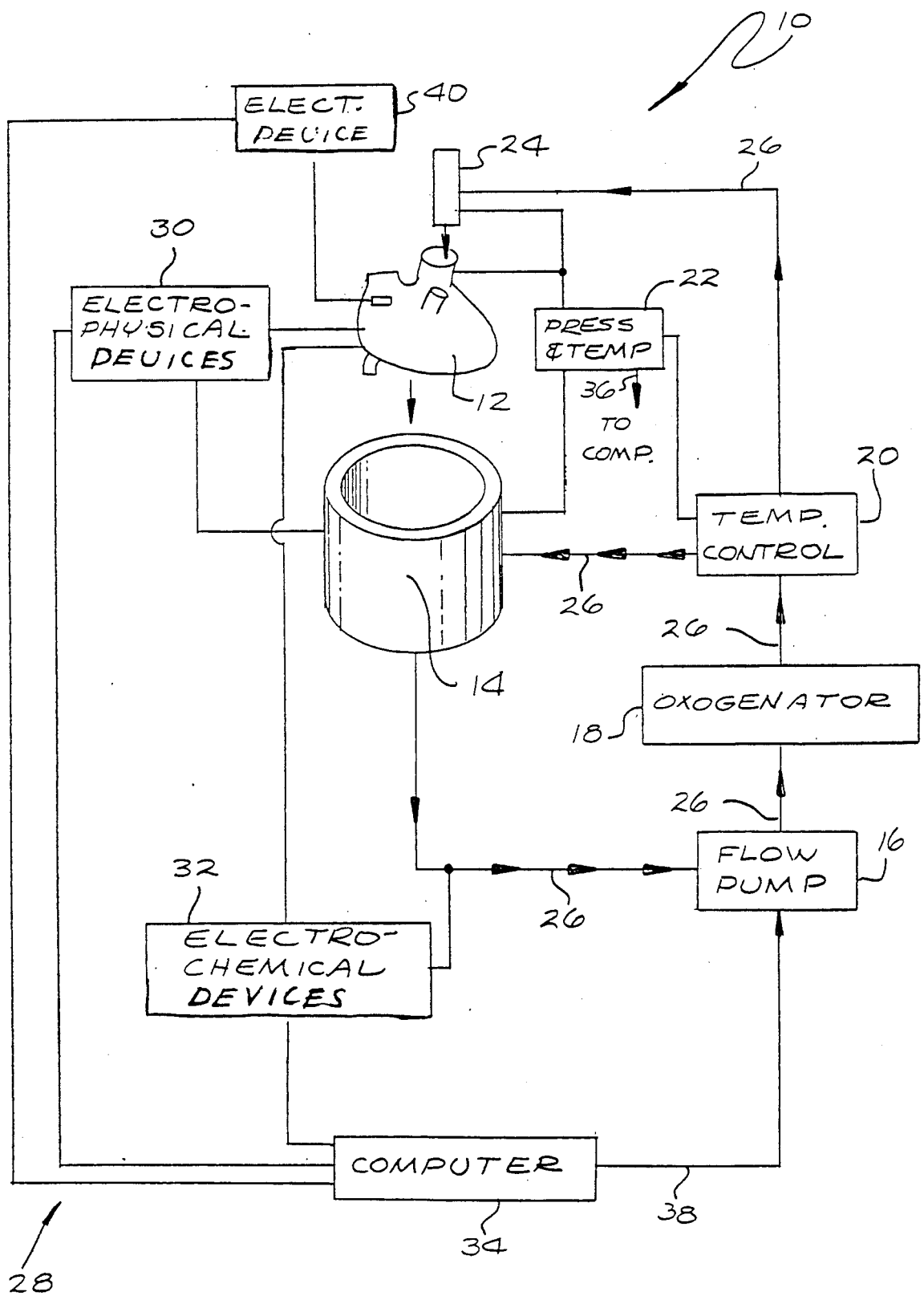
FIG. 1 is a schematic illustration of an apparatus in accordance with an embodiment of the invention.

The invention is directed to apparatus and methods for preserving animal organs in a viable state. By viable state it is meant to maintain the organ in a condition whereby the normal metabolic activities of the organ continue, albeit at a lower rate. Furthermore, for purposes of this discussion the term "organ" is meant to include not only typically thought of organs, e.g. the heart, liver, kidney, brain, etc., but also limbs, e.g. arms and legs, and tissue.

Generally, the apparatus of the invention includes various devices for circulating a perfusate through the organ. These devices include those presently available devices for pumping, oxygenating, defoaming and regulating the pH of the perfusate, as well as devices for regulating the temperature of the perfusate, and thus organ, within a prescribed temperature range. The present apparatus further includes various devices which monitor and control of the organ transmembrane potential.

The term transmembrane potential is typically used in reference to cells. Cells possess a membrane potential which will vary depending upon the conditions under which the cell is subjected. The conditions under which a cell is subjected affects the operation of the cell. That is, under normal resting conditions a cell will possess a given potential, usually a narrow potential range. However, this potential can be rapidly and dramatically depolarized to have a profound affect upon that particular cell, as well as the entire organ. This depolarization will make that particular cell more susceptible to excitation by establishing an action potential. That is, the cell activity will dramatically increase by the establishment of this action potential.

While transmembrane potential is generally used in reference to cells it has recently been observed that organs also exhibit a similar type electrical potential. That is, a resting heart cell is known to possess a potential having an internal negative charge. The resting heart also possesses a potential having an internal negative charge, though not always within the same potential range.

In general terms, this potential involves the polarization of electrical charge along the cell membrane, thus the term transmembrane potential. There are numerous factors which affect the polarization of this potential. One particular factor is the distribution of ions, anions and cations, along opposing sides of this membrane. This particular factor is used by the apparatus and methods of the invention to monitor and regulate the transmembrane potential of a particular organ, as will be discussed more fully herein.

For the purposes of this discussion "transmembrane potential" includes various types of potentials. That is, transmembrane potential includes that potential resulting from a difference between an organ internal and external charge (hereinafter "transorgan electrical potential"), that potential resulting from a difference in charge between two internal areas of an organ (hereinafter "intraorgan electrical potential"), and that potential resulting from a difference in charge between two different organs (hereinafter "interorgan electrical potential"). However, for the purposes of the invention reference herein to transmembrane potential shall mean inclusively transorgan and intraorgan electrical potential.

Referring now to FIG. 1, a schematic illustration of an apparatus in accordance with an embodiment of the invention can be seen at 10. The apparatus 10 will be discussed in reference to a heart 12, however, it is to be understood that the instant invention may be used to preserve the viability of any other organ, e.g. liver, kidney or brain as well as a limb, e.g. an arm or finger.

Apparatus 10 includes a vessel or chamber 14 into which is supported the heart 12. This chamber 14 may be of any suitable construction. The chamber 14 is constructed to hold not only the heart 12 but also a sufficient amount of a suitable perfusate to substantially cover the heart 12.

For the purposes of this discussion the term perfusate is meant to include typical perfusate compositions which include the necessary nutrients for that organ being preserved, as well as, the necessary electrolytes and other necessary constituents and other fluids typically used in apparatus and methods for preserving the viability of organs. In place of typical perfusate compositions the apparatus may utilize plasma or whole blood which would function as the perfusate. Thus for the purposes of this discussion the term perfusate shall mean any fluid useful for maintaining the viability of an organ in a method and apparatus as discussed herein.

When the organ to be preserved is an arm or other relatively large limb the apparatus 10 will further include a platform, not shown, upon which the limb is rested. Generally, the platform and chamber 14 will be constructed adjacent to each other and in such a manner to allow the resting of the limb on the platform and the positioning of the severed end attached to a system for circulating the perfusate.

The apparatus 10 also includes other devices which are selectively connected to the heart 12 and/or chamber 14. In particular, the apparatus 10 includes various devices which circulate a perfusate through the heart 12 and chamber 14. These devices include a flow pump 16, oxygenator 18, temperature control device 20 and temperature/pressure monitoring device 22. These devices are those typically utilized for circulating a perfusate though the heart 12 and chamber 14.

The circulation of the perfusate between the various devices 16, 18 and 20 to the heart 12 and chamber 14 is schematically illustrated by the pathway, indicated generally at multiple locations at 26. The direction of perfusate flow through this pathway 26 is indicated by the arrows.

The pathway 26 is typically constructed from surgical grade tubing. This tubing should meet USP Class VI criteria, and in any event should be formed from a material which will not adversely react with the perfusate being circulated therethrough. Typically diameters for useful tubing is from 1/16" to 1".

The flow pump 16 may be any suitable pumping device, such as those used with presently available systems as described in the above incorporated references. For example, the flow pump 16 may be adapted to circulate the perfusate through the apparatus at a constant fluid pressure, or be of the pulsating type which pumps discrete quantities of the perfusate at alternating periods of time.

In accordance with a preferred embodiment of the invention the flow pump 16 is of the type which continuously pumps the perfusate through the apparatus at a constant pressure. This flow pump 16 is a suitable self-priming, non-pulsating pump constructed to provide micro-metering of the perfusate fluids. The preferred flow rate for such a device is from about 3 to 5000 milliliters per minute.

The oxygenator 18 is any suitable device or devices which diffuses oxygen into the perfusate while removing carbon dioxide. For example, the oxygenator 18 may include a membrane oxygenation system which contains a membrane adapted to separate an oxygen carried gas from the perfusate. This type of system diffuses oxygen across the membrane into the perfusate. The oxygen diffuses into the perfusate displacing carbon dioxide. The oxygenator 18 may also be a bubble oxygenator. This type of device connects a tube to the chamber 14 through which an oxygen carrying gas is delivered to the perfusate. The oxygen is absorbed by the perfusate as the gas passes therethrough.

The oxygenator 18 of the invention may also include any necessary filters, not shown, to remove waste products, entrapped air or other material being carried by the perfusate. The oxygenator 18 will also include devices, not shown, for measuring the presence of oxygen and carbon dioxide in the perfusate, typically at points prior to oxygenation and after oxygenation, to allow for a monitoring of the amount of oxygen being delivered to the heart 12.

The flow pump 16 and oxygenator 18 devices may be of any suitable construction typically used in presently available systems, such as those discussed in the above incorporated references. These devices are not critical in regards to discussing the invention and will thus not be described in any further detail herein.

The temperature control 20, which will be discussed in greater detail herein, is any suitable device or devices which are adapted for regulating the temperature of the perfusate to within a desired range. This temperature control 20 will typically include heat transfer mechanisms through which the perfusate is circulated for either transferring heat to the perfusate or removing heat therefrom.

The amount of heat transferred to or removed from the perfusate is a function of that temperature desired for the heart 12 or other organ. The heart 12 temperature is continually monitored, with the temperature control 20 determining that temperature of the perfusate necessary to obtain the desired temperature of the organ. Typically, such a determination is performed by a computer, as shown in FIG. 1 at 34, which is typically included in the apparatus 10. The computer 34 will receive information regarding the heart 12 temperature and the perfusate temperature at various locations along the circulation route, and from this information determine the amount of heat to be transferred to or removed from the perfusate by the temperature control 20 in order to achieve the desired temperature for the heart 12.

Specifically, the temperature of the perfusate is directly measured by the pressure/temperature device 22, which includes various temperature probes selectively positioned in the heart 12 and chamber 14 for measuring the heart 12 and perfusate temperature these points. This information, which is converted into electronic digital signals, is then transferred to the computer 34 which includes suitable electronic circuitry for receiving the signals and suitable programming for calculating the temperature at which the perfusate should be maintained in order to achieve the desired temperature of the heart 12.

The computer 34 also includes suitable electronic circuitry for generating signals which are transmitted to the temperature control 20. The control 20 is design to operate in response to these signals and regulate the perfusate temperature flowing therethrough.

As will be described more fully herein the placement of the temperature sensing probes is critical in order to precisely regulate the temperature of the organ. A variation in temperature of the heart 12, or any organ, will directly affect the viability of that organ. In particular, when the organ temperature is too high the organ metabolic rate is so high that the amount of oxygen being supplied is not sufficient. That is, the metabolic rate increases so that the organ consumes oxygen at a rate greater than the rate at which the perfusate carries oxygen. This results in damage to that organ. When the temperature becomes too low the amount of oxygen radicals increase sufficiently such that such radicals becomes toxic to the organ.

Thus the range of temperature at which the organ is maintained is critical. It has been determined that such temperatures should not exceed 37° C., and should not drop below 5° C. More particularly, such temperatures should be maintained in a range of from about 15° C. to about 27° C.

In accordance with a preferred embodiment of the invention the apparatus 10 further includes a self-regulating pressure valve 24. This pressure valve 24, as will be described in detail herein, is coupled to the heart 12 at that location at which the perfusate is entering the heart 12. In the illustrated embodiment the valve 24 is coupled to the heart 12 aorta. The valve 24 is adapted to release perfusate when the pressure in the heart 12, as caused by the flow of the perfusate and vascular resistance, exceeds a predefined limit. This allows the pump 16 to be a continuous circulating device while minimizing the potential of damage to the heart 12 from an undesirable increase in fluid pressure.

This pressure valve 24 may further be constructed to be connected to the pressure/temperature monitoring device 22 to allow for the monitoring of the pressure in the valve 24. The pressure as measured by the monitoring device 22 may be used by the apparatus 10 to regulate the perfusate flow rate of the flow pump 16. That is, the computer 34 will be connected to the monitoring device 22, which device 22 generates appropriate signals in response to the pressure which are transmitted to the computer 34. The computer 34 includes suitable programming which utilizes these signals representative of the pressure in pressure valve 24 to initiate instructions for regulating the flow rate from the flow pump 16.

The apparatus 10 may also include other presently used devices for preserving the viability of an animal organ. For example, the apparatus 10 may also include devices for effecting the removal of waste products from the perfusate, devices for adding nutrients to the perfusate and devices for defoaming the perfusate. None of these devices have been illustrated and are not critical to the discussion of the invention.

In accordance with the invention the apparatus 10 includes various devices for monitoring and regulating the transmembrane potential of the heart 12, and specifically the electrophysical and electrochemical characteristics of the heart 12, or other suitable organ. These devices are grouped in a system generally seen at 28.

It has been observed that altering the electrochemical and electrophysical properties of the organ can depolarize the transmembrane potential to such an extent that the threshold level is exceeded which establishes an action potential for that organ. That is, any fluctuation of the potential polarization will increase the excitability of that organ. This will directly or indirectly affect the viability of that organ.

As used herein "electrophysical characteristics" generally refers to the electrical properties of electrical potential or voltage, resistance, conductance and impedance associated with the physiologic processes of the organ being stored in the apparatus 10. Furthermore, these electrical characteristics are determined by monitoring not only the electrical properties of the heart 12, or other organ, but also of the perfusate and the apparatus 10, in general. Thus, as will be described more fully herein the measurement of the electrophysical characteristics of the perfusate and of the apparatus 10 are relevant in regards to determining a precise measurement of the actual electrophysical characteristics of the organ.

In particular, the specific electrophysical characteristics monitored include among other electrical properties the difference in charge distribution, i.e. conductance, resistance, impedance and voltage, between various portions of said organ and the extraneous electrical stimuli interference.

As used herein "electrochemical characteristics" refers to those characteristics concerning the electrochemical reactions which are effected by electricity. These characteristics generally include the cellular electrochemical activity of the organ stored in the apparatus 10, e.g. the cellular pH which is monitored by measuring and regulating the perfusate pH, and the cellular ion concentrations. Specifically, the characteristics being measured concern the movement of relevant ions across the cellular membranes, which ion movement is effected by the electrical potential. Thus the measurement of the electrochemical characteristics provides an understanding of the transmembrane potential and other electrical properties of the particular stored organ.

In particular, the apparatus 10 includes various devices for monitoring the ratio of intracellular to extracellular concentration of potassium ions, the extracellular concentration of sodium ions, and the pH of said perfusate. The system 28 may also include various devices for regulating these electrochemical properties, e.g. a device for regulating the perfusate pH or perfusate potassium or sodium levels.

More specifically, the specific devices for monitoring and regulating the electrophysical characteristics of the heart 12, are indicated at 30 and 40, respectively, while those devices for monitoring and regulating the electrochemical characteristics are seen generally at 32. These devices 30, 40 and 32, which will be described more fully herein, transmit such measured properties to the computer 34 which includes suitable programming for initiating the activation of the particular electrophysical and electrochemical regulating devices.

As stated, the system 28 includes one or more devices for regulating the electrophysical characteristics of the heart 12, which devices are seen generally as device 30 and stimulation system 40. These devices perform different operations. In particular, the device 30 is operated to electrically stimulate the heart 12 for correcting any variance in the heart 12 electrophysical characteristics. This electrical stimulation readjusts the electrical potential of the heart 12 to its normal resting state.

When the apparatus 10 is being specifically used for storing hearts the system 40 will include devices specifically for electrically stimulating the heart 12 for correcting certain conditions which are only particular to the heart 12. These devices, which will be described in greater detail herein, electrically maintain the heart 12 beats or pulse rhythm and also electrically adjust undesirable fibrillation of the heart 12. As will be described, these particular devices are standard for their intended purpose but have not heretofore been utilized in an apparatus as the instant invention.

In particular, the computer 34 has been previously programmed to include defined limits for these properties. In particular, the computer 34 includes the electrophysical properties of resistance, conductance, impedance and voltage of the organ in its natural state. If the properties being measured while the organ is being stored in the apparatus 10 significantly vary from the properties of such organ in its natural state the computer initiates a readjustment of these properties by operating the device 30, and/or one or more of the stimulating devices 40.

The specific devices useful for monitoring and regulating the various electrophysical and electrochemical properties of the heart 12 will now be discussed in greater detail with reference to FIGS. 2-6.

Figure 2:
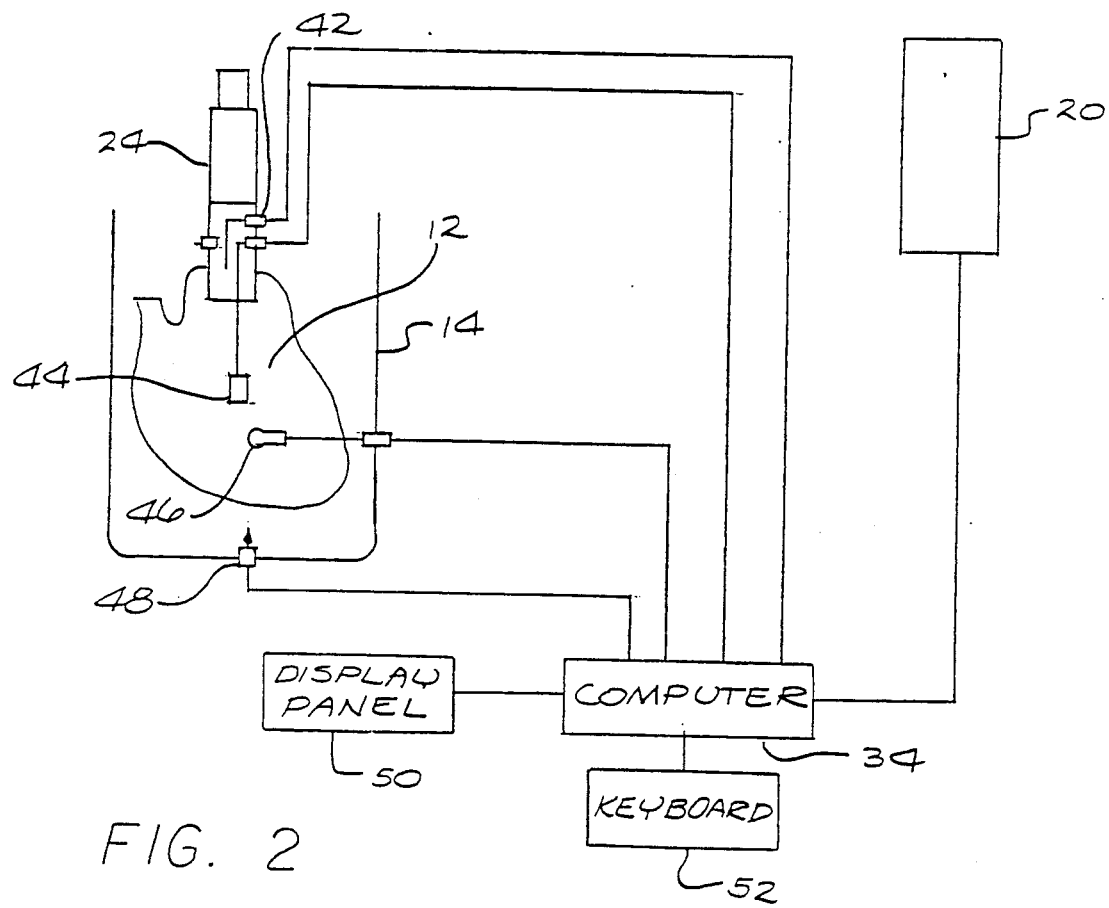
FIG. 2 is a schematic illustration of a preferred temperature monitoring system for incorporation into the apparatus of the invention.

Referring in particular to FIG. 2, a schematic illustration of a preferred temperature monitoring portion of the pressure/temperature device 22, as seen in FIG. 1. The temperature monitoring portion of the device 22 generally includes a plurality of temperature probes. In accordance with a preferred embodiment of the invention a first of these probes 42 is located to contact the perfusate entering the self-regulating valve 24. A second and third of these probes are independently located to measure the temperature inside and outside of the heart 12, as seen respectively at 44 and 46. A fourth probe 48 is located in the chamber 14 to measure the temperature of the perfusate in the chamber 14.

All four of these probes are electrically coupled over communication lines to the computer 34, which includes suitable indicators of these temperatures, if desired, on a display panel 50. The computer 34 is suitable programmed in accordance with various known algorithms to determine the actual temperature of the heart 12 by eliminating from the temperature measured by the probe 46 the temperature of the surrounding perfusate as measured by the probe 48. Further the temperature of the perfusate entering the heart 12 as measured by probe 42 is eliminated from the internal temperature of the heart 12 as measured by the probe 44. In this fashion, the temperature at which the heart 12 is being maintained is determined by eliminating the background temperatures of the perfusate.

Once the computer 34 has completed the various calculations to determine the temperature at which the heart 12 is being maintain this is compared to a predefined desired maintenance temperature. This desired temperature can be entered directly into the computer 34 through a keyboard 52 electrically connected to such computer 34. If the heart 12 is not being maintained at this desired temperature the computer 34 initiates another set of computations to determine at which temperature the perfusate should enter the heart 12 in order to obtain the desired temperature. The computer 34 then communicates with the temperature control 20 to regulate the cooling or heating process of the perfusate as carried out in this control 20.

As stated, this temperature should not exceed 37° C., nor drop below 5° C., and preferably should fall in the range of from about 15° C. to about 27° C.

Referring now to FIGS. 3 through 6 schematic illustrations of the system 28 and of specific electrical monitoring and stimulating devices will be described. In particular, the system 28 which monitors and regulates the electrophysical and electrochemical characteristics of the heart 12 will now be described in greater detail. The various devices to be described herein for incorporation into the system 28 are, unless specified, are presently available devices, which in and of themselves not critical to the discussion of the invention. The invention is primarily directed to an apparatus and method for preserving the viability of animal organs which incorporates such devices for monitoring and regulating the electrochemical and electrophysical characteristics of the organ. Heretofore such monitoring and regulating was not performed by available organ preservation apparatus.

The system 28 includes, among others, devices for monitoring certain electrochemical characteristics of the perfusate. These devices allow for a determination of how the perfusate may be affecting the electrophysical and electrochemical characteristics of the organ, i.e. heart 12, or an indirect measurement of the electrophysical and electrochemical characteristics of the heart 12.

All of these devices will be electrically connected to the computer 34 to allow for an ongoing calculation of the electrophysical and electrochemical characteristics. That is, the computer 34 includes suitable programming in accordance with desired algorithms which utilize the various properties being measured by these devices to determine if the electrophysical and electrochemical characteristics of the heart 12 are varying from its natural state.

The various electrical connections of each of the devices to be discussed are schematically illustrated by the lines connecting the various devices to the computer 34. Other ones of these lines illustrate the electrical connections between these devices and the chamber 14 or heart 12. These latter electrical connections concern the various probes used to measure the desired electrophysical and electrochemical properties, as to be defined herein, of the heart 12 or perfusate contained in the chamber 14 or of the apparatus 10 itself.

In particular, the system 28 includes a pH monitoring device 54. This pH monitor 54 may be any suitable device capable of measuring within the range of 0.00 to 14.00 pH and in particular within a predefined physiological range for each tissue and organ, and in particular within the range of 7.3 to 7.5 for a typical heart. The monitor 54 includes probes which are positioned in contact with the perfusate located in the chamber 14 and the arterial input and various output sites of the organ.

The pH monitoring device 54 should preferably include, or be connected to a suitable device for regulating the pH of the perfusate, with such a device being indicated at 55. Presently available organ preservation apparatus utilize a pH regulating device 55 which regulates the perfusate pH by introducing carbon dioxide into the perfusate. However, the pH regulating device 55 may be any suitable device which functions to regulate the pH by introducing any suitable non-toxic chemical into the perfusate.

The pH monitor 54 will be connected to the computer 34 and include suitable electronic circuitry for generating appropriate digital signals. The computer 34 utilizes these digital signals to determine if the measured pH falls within a previously defined pH range. If the measured pH falls outside of this defined range then the computer 34 generates signals which are transmitted to the pH regulating device 55 to initiate the operation of the pH regulating device 55.

The system 28 should also include a device for monitoring the extraneous electromagnetic interference present in the apparatus 10. This type of device, which is generally referred to at 58, provides numerous functions. One such function is to provide a reading of the background electrical noise being generated by the various devices of the apparatus 10. This background noise, which is transmitted as appropriate digital signals to the computer 34, is utilized in calculating the electrophysical characteristics of the organ, e.g. heart 12. That is, this device 58 measures electrical interference or background noise which is eliminated from any calculations of the electrophysical characteristics of the organ.

Of more importance is that by measuring the extraneous electromagnetic interference the possibility of electrocautery damage to the heart 12 is minimized, which is one of the most hazardous iatrogenic stimuli to the heart 12. This interference monitoring device 58 is electrically coupled to the computer 34 and continuously supplies the computer 34 with information regarding this electromagnetic interference in the form of digital signals. The computer 34, which was previously programmed with a defined limit for such interference, will initiate a safety procedure when this defined limit is exceeded.

For example, the computer 34 may be suitably programmed to activate an alarm when the defined limited is exceeded, or may be suitably programmed to turn off certain devices of the apparatus 10 when the defined limit is exceeded.

The system 28 further includes various devices for monitoring desired chemical properties, including suitable devices for measuring and determining the concentration, either intracellular, extracellular or both, of certain ions. In particular, the system 28 includes one or more devices for measuring the ratio of the intracellular to extracellular potassium concentration, and for measuring the extracellular concentration of sodium ions. An example of such a suitable device, seen generally at 60 is an ion selective microelectrode.

The information obtained by these ion measuring devices 60 are communicated to the computer 34 which then performs a desired mathematical operation upon this information to determine if the concentrations of these ions fall within previously defined levels. That is, the computer 34 is previously provided with a desired ratio range for the intracellular to extracellular potassium concentration, and if the measured ratio falls outside of this range the computer 34 initiates corrective actions. As will be discussed herein, these corrections include generating and delivering an electrical stimulation to the heart 12, or the activation of devices for increasing or decreasing the level of certain ions, e.g. potassium or sodium, in the perfusate.

As stated, the purpose of the system 28, and thus the apparatus 10, to mimic as close as possible the natural electrophysical and electrochemical characteristics of the organ. This involves regulating the electrochemical environment of the organ as well as the electrophysical environment of that organ. As already stated, one possible manner of regulating the electrochemical environment of the organ is by regulating the pH of the perfusate flowing through the organ and contained in the chamber 14 in which the organ rests.

The electrophysical characteristics of the organs will be monitored by including in the system 28 suitable devices for monitoring and regulating the electrical potential of the heart 12, or other organ. The precise type and number of such devices will depend upon the particular organ being preserved in the apparatus 10. In particular, there are various different types of known devices which are presently being used to measure the electrical activity, that is potential, of different types of organs.

The system 28 will include one particular device for measuring and regulating the electrophysical properties of the heart 12, or for that matter any organ. This device operates to measure the internal and external electrophysical properties of conductance, impedance, resistance and voltage of the organ, in order to determine the potential of the organ.

In particular, this particular device, which is seen at 62, measures the internal electrophysical properties of the organ versus the electrophysical properties of the perfusate. While presently available devices may be suitable for this purpose, a particularly preferred device which is not presently available is shown in greater detail in FIG. 4. It should be noted that the device 62 illustrated in FIG. 4 functions to both monitor the electrophysical properties of the heart and also to regulate such properties by generating a suitable electrical current which is delivered to the heart.

Figure 4:
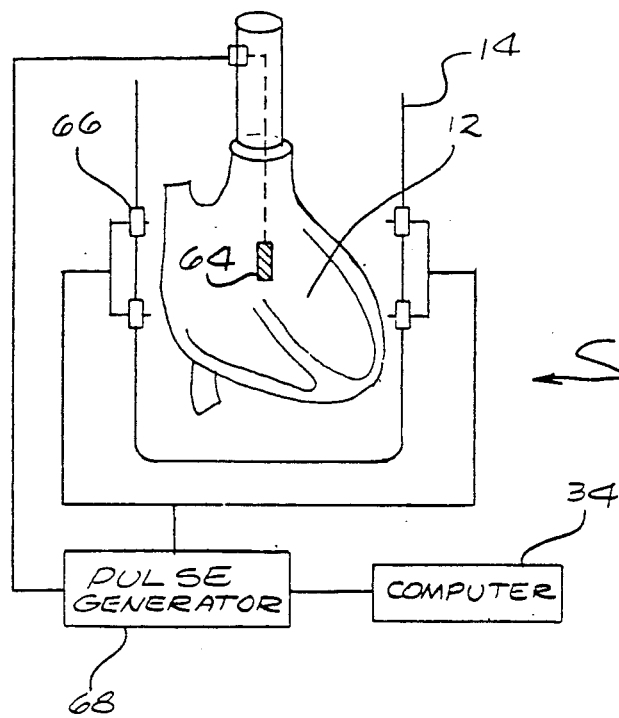
FIG. 4 is a schematic illustration of an electrical stimulator used in the electrophysical and electrochemical monitoring and regulation system in accordance with an embodiment of the invention.

Specifically referring to FIG. 4, the device 62 monitors the electrophysical characteristics of both the organ and the perfusate, that is the conductance, voltage, impedance and resistance.

This device 62 includes one or more electrodes located for contacting the perfusate in the chamber 14, which are indicated generally at 66. These electrodes should be able to monitor the resistance in the range of 0.2 ohms to 2.5 megohms, and the conductance within the range of 0.01 micro mhos to 2.5 mhos. The electrophysical properties of the heart 12 are measured by an electrode 64 which is located inside the heart 12, as seen in FIG. 4. This electrode should also be able to measure the resistance in the range of 0.2 ohms to 2.5 megohms, and the conductance within the range of 0.01 micro mhos to 2.5 mhos.

The electrodes 64 and 66 are electrically connected to a device which includes suitable electronic circuitry for converting the measurements to digital signals transmitted to the computer 34. These signals are then operated on by suitable programming to determine the difference between the electrical properties of the heart 12 and of the perfusate, which provides the electrophysical properties of conductance, resistance, voltage and impedance for the heart 12.

These electrophysical properties are compared to the previously defined electrophysical properties for a resting heart 12 to determine any variance of such properties. If a variance is determined than the computer 34 initiates the operation of suitable electrical stimulating devices.

In particular, the computer 34 will initiate the generation of electrical current which is delivered to the electrodes of the device 62. As stated this device 62 includes a plurality of electrodes connected to the chamber 14 and heart 12, that is electrode 64 located inside the heart 12 and the plurality of electrodes 66 located along the interior surface of the chamber 14.

These electrodes 64 and 66 not only monitor the various electrophysical properties but are also electrically connected to a pulse generator 68. This generator 68 is operated by signals received from the computer 34 to deliver an electrical current of 1 millivolts to 80 volts, 0.001 to 15 amps, to the electrodes 64 or 66, which then passes through the heart 12 to the other of such electrodes 64 or 66. Thus this device 62 functions to both monitor and to regulate specific electrophysical properties of the heart 12, or for that matter any other organ.

The precise amount of voltage delivered to the electrodes 64 and 66 is dependent upon the amount of voltage necessary to adjust the potential of the heart 12. That is, if the potential is calibrated to vary 50 millivolts from the normal state potential then the device 62 delivers the required electrical stimulus to the heart 12. Thus, the precise amount of voltage being delivered is specifically dependent upon that amount necessary to correct the potential to the normal resting state potential. It should be noted that the resting state potential for each organ being stored should be determined prior to removing that organ from the donor. This potential is then entered into the computer 34.

When an organ other than a heart is being preserved one or more of the electrodes 64 can be positioned internally within the organ, with a suitable number of electrodes 66 located in the chamber 14. Furthermore, for certain organs it may be undesirable to locate an electrode inside the organ. Under these circumstances a plurality of electrodes should be arranged to ensure that an electrical current will pass through the respective organ to provide the desired electrical stimulation of such organ.

Figure 3:
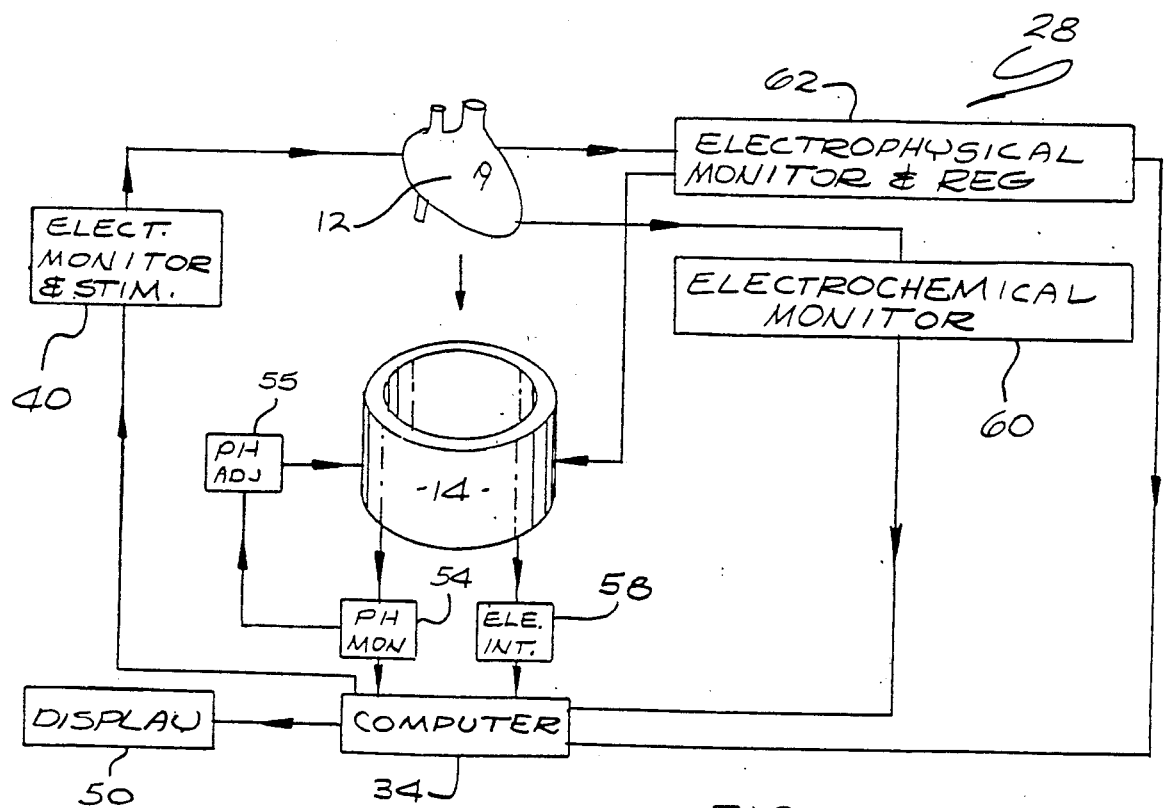
FIG. 3 is a schematic illustration of an electrophysical and electrochemical monitoring and regulation system in accordance with an embodiment of the invention for incorporation into the apparatus of the invention.

The system 28 may also include other devices for monitoring and regulating the electrophysical properties of various types of organs, and in particular, when the organ is a heart. These devices are generally indicated in FIG. 3 as a system 40.

For example, the system 40 may include a device which continuously monitors a heart's cardiac rhythm for analyzing the fibrillation activity of the heart. As known in the art, ventricular fibrillation is the absence of isoelectric potential segments, and is generally defined as a fine, rapid, fibrillary movement of the ventricular muscle, in comparison to normal contraction. Any suitable device which would monitor and indicate the onset of fibrillation can be used with the system 40. This device would be electrically connected to the computer 34, which would initiate a suitable corrective response upon the onset of fibrillation. As will be discussed herein, these corrections include generating and delivering an electrical stimulation to the heart 12.

Other suitable devices which may be used when monitoring the electrophysical characteristics of a heart include electrocardiogram and electrocardiophonogram devices. The former device monitors the heart currents by recording the potential of the electrical currents traversing the heart, which currents are known to initiate heart contraction. That is, it is known that such electrical currents will traverse through the heart just prior to each beat of the heart. The latter type of devices measure and record the auditory sounds of the heart.

When the apparatus 10 is being used to preserve the viability of an organ other than the heart 12, the system 40 may include other suitable devices which will be used to measure various electrical properties of that organ. For example, electromyogram devices may be used to measure the somatic electric currents associated with muscular activity when the organ being preserved is for example a limb or other organ in which muscular activity is the central function When the organ being preserved includes surface tissue such as skin the system 40 may include one or various types of devices which measure the electrical property of such surface tissue as measured by the alteration of the surface tissue resistance.

When the organ is a brain the system 40 may include one or more of various devices for measuring the electrical activity of the brain, i.e. electrocorticogram (cerebral cortex) or electroencephalogram (measurement of brain alternating current). It can thus be seen that there are various devices useful in the practice of the present invention for measuring various electrical properties of an organ being preserved.

As stated the system 40 may further include suitable devices for generating and delivering electrical stimulation to the heart 12 or other suitable organ when it is determined, by the computer interfacing with the various monitoring devices discussed above, that corrective measures are necessary. This stimulation system 40 will include those devices suitable for providing the desired electrical stimulation to that organ being preserved. That is, for each different organ, a differently configured stimulation device will be needed, in particular, the probes used to deliver such generated electrical voltage will be differently located in each organ. The precise location for such probes can be determined for each selective organ.

Figure 5:
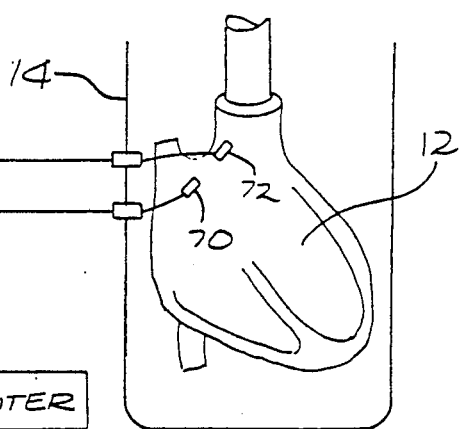
FIG. 5 is a schematic illustration of an electrical device coupled to a heart for stimulating the heart rhythm used in an embodiment of the invention for the storage of hearts.
Figure 6:
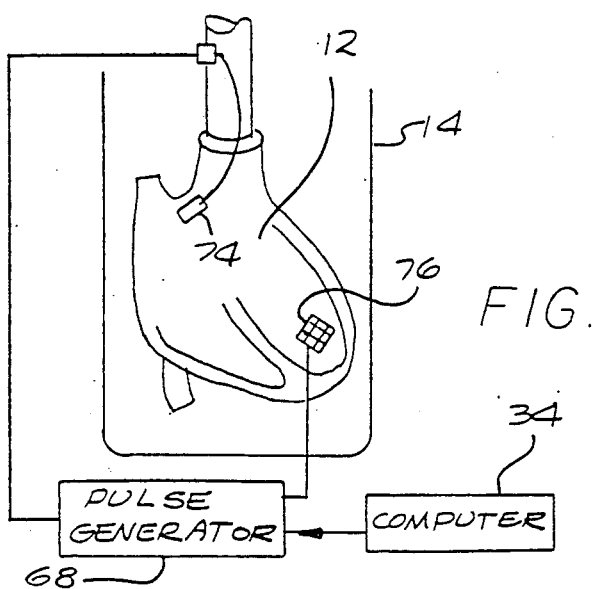
FIG. 6 is a schematic illustration of an electrical device for correcting fibrillation of a heart being stored in the apparatus of the invention.

Referring now to FIGS. 5 and 6, specific devices which may be included in the system 40 for providing the necessary electrical stimulation to the heart 12 are illustrated. The importance of these additional devices for use in stimulating the heart is a result of the association of the heart's viability and its electrical activity.

FIG. 5 illustrates a standard device used to generate electrical stimulation for ensuring the proper beating rhythm of the heart. Such devices are generally referred to as pace makers. The electrodes of this device, with the anode indicated at 70 and the cathode indicated at 72, are electrically coupled to the pulse generator 68. The anode 70 and cathode 72 are suitably located to ensure that the generated current will pass through the excitable myocardium. That is, the electrodes 70 and 72, will typically be positioned at opposing sides of the excitable myocardium. The operation of a device such as this is well known in the art and will not be discussed any further herein.

FIG. 6 illustrates a standard device used to correct heart fibrillation. Again, this type of device is well know in the art and will not be discussed in any great detail herein. Generally, this type of device includes two electrodes, with a first electrode 74 located inside the right ventricular and a second electrode 76 located near the vena cava. These electrode 74 and 76 are also connected to the pulse generator 68 which generates a suitable current of a desired voltage to such electrodes as is well known in the art.

It can thus be seen that the system 28 will include one or more devices for stimulating one or more different types of organs, and in particular the device 62, as well as other suitable devices which make up the system 40.

The system 28, or apparatus 10, may also include other devices which regulate, for example, the ion concentration of the perfusate. It is known that ions will diffuse from regions of high concentration to lower concentration. Thus if the ion measuring devices 60 indicate an improper ratio of intra- to extra-cellular concentration of potassium, or if the electrophysical characteristic monitoring device 30 measures an improper potential, then a suitable device may increase or decrease the perfusate concentration of potassium sodium ions to cause a redistribution of the ion concentration by appropriate diffusion.

As stated above, the apparatus 10 of the invention also includes a self-regulating pressure valve 24. This valve 24 will now be described in greater detail with reference to FIG. 7. The self-regulating pressure valve 24 includes a generally cylindrical body 78. This body 78 is constructed with two passageways 80 and 82, which passageways are separated by a partition 84 defining an aperture 86. The body 78 also has first and second ends 88 and 90, with the passageway 80 opening at the end 90 and passageway 82 opening at end 88. End 88 is fitted to the organ, as illustrated the heart 12 aorta.

The valve 24 further includes to spherical valve members 92 and 94 dimensioned to slidably fit in the passageway 80. These two spherical valve members 92 and 94 are resiliently urged away from each other by a spring 96 positioned in the passageway 80 therebetween.

The aperture 86 and spherical valve member 92 are dimensioned so that when brought into engagement with each other they will cooperate to seal the passageway 80 from passageway 82. The end 90 can be fitted with a cap, seen at 98, upon which the spherical valve member 94 comes to rest. Thus, under normal load the spherical valve member 92 is urged by the spring 96 into engagement with the partition 84 and cooperate with the aperture 86 to seal the passageway 80 from the passageway 82.

The passageway 82 includes one or more connections, with one such connection being seen at 100, to allow for the entrance of a perfusate therein. As the perfusate enters this passageway 82 it will flow into the heart 12 via the aorta. The self-regulating pressure valve 24 is designed to maintain a predefined optimal constant perfusion pressure, that is, the pressure is sufficiently high to optimally perfuse the organ and sufficiently low to prevent pressure-induced damage to the organ. If either the perfusate flow rate and/or the resistance to flow in the organ increases, the expected consequence of an increase in pressure does not occur because perfusate entering into passage 82 moves the spherical valve member 92 into the passageway 80 against the opposing urging action of the spring 96 to allow for the passage of the perfusate from passageway 82 into passageway 80.

The body 78 is further formed with one or more openings 102 which communicate with the passageway 80 at a location adjacent to the spherical valve member 92. When the spherical valve member 92 is moved into the passageway 80, so as to disengage the aperture 86, the perfusate entering the passageway 80 can exit through these openings 102.

The precise pressure at which the self-regulating valve 24 will cause a release of excess perfusate is dependent upon the strength of the spring 96. A further modification of the valve 24 to allow for an adjusting of this release pressure is obtained by substituting a reciprocating cap for the stationary cap 98. That is, cap 98 is constructed to be slidably mounted in the end 90, such that as the spherical valve member 92 is being moved inward the passageway 80 the cap 98 will move in the same direction by the urging action of the spherical valve member 94.

A still further modification includes constructing the valve body 78 from a clear plastic or glass material and providing the body 78 or cap 98 with a graduation scale 104 at a location adjacent to the end 90. By further locating the either of the body 78 or cap 98 with a marker 106 which is positioned to indicate a location of the graduation scale the self-regulating valve 24 is adapted to indicate the perfusate fluid pressure being delivered to the heart 12.

It should be noted that the self-regulating valve 24 can be connected to any other suitable organ, and may be used either singularly or in combination with other self-regulating valves when the organ being preserved is coupled to more than perfusate line.

The operation of the apparatus of the invention involves first determining the various electrophysical properties of that particular organ in its natural state. That is, the resistance, impedance, conductance and voltage of that particular organ should be determined. This information is used as a base line against which the measured properties of such organ when being stored in the apparatus 10 can be compared against. The organ is then surgically removed and situated in the chamber 14. The various electrodes are inserted into the particular organ to arrange the same as described herein. Furthermore, the circulation system, that is, those devices which oxygenate, pump and control the perfusate temperature are connected to the organ. This involves connecting the tubing of such devices, and preferably the self-regulating pressure valve, to the organ.

After the organ is fully connected into the apparatus 10 the various devices of the apparatus 10 are activated. These devices will monitor and regulate the various electrophysical and electrochemical properties of the organ, as discussed above. For example, the various electrophysical properties of the organ will be constantly monitored with the appropriate devices operated to provide the necessary electrical stimulation.

Experiments were conducted using an apparatus in accordance with the invention. These experiments involved removal of viable hearts from 6 canines, 1 sheep and 1 pig, and connecting these hearts to the apparatus. Specifically, the hearts were removed in accordance with standard Transplant Heart Surgery Protocol and first connected to a circulation system as described herein, including a self-regulating valve, as described herein.

The temperatures of the hearts at initiation of the experiments were from 15.3° C. to 20.5° C. During the experiment each heart was maintained at a temperature of from 12.5° C. to 37.5° C. The electrophysical and electrochemical properties of each heart were maintained to simulate that heart's normal resting properties. Of the 8 hearts used, 5 remained viable for periods of 9 to 21 hours. The remaining 3 hearts remained viable for less than 6 hours. Again, by viable it is meant that the hearts remained beating for the specified periods of time.

While the preferred embodiment has been described and illustrated, various substitutions and modifications may be made thereto without departing from the scope of the invention. Accordingly, it is to be understood that the present invention has been described by way of illustration and not limitation.

What is claimed is:

1. An apparatus for maintaining viability of animal organs for a period of time sufficient to enable the use of such organs for transplantation and medical research, said apparatus comprising:

chamber means for receiving and supporting the organ;
  perfusate circulating means positioned and arranged so as to regulate supply of a perfusate to the organ and to collect perfusate from the organ;
  temperature regulating means connected to said perfusate circulating means and positioned and arranged so as to maintain the temperatures of the organ and the perfusate within predetermined ranges;
  oxygenator means connected to said perfusate circulating means for maintaining an oxygen level in the perfusate supplied to the organ by said perfusate circulating means within a predetermined range;

electrochemical monitoring means connected to said perfusate circulating means for monitoring electrochemical characteristics of the organ and the perfusate and for maintaining the monitored electrochemical characteristics within predetermined ranges, the electrochemical characteristics comprising the ratio of intracellular to extracellular concentration of potassium ions, the extracellular concentration of sodium ions, and the pH of the perfusate; and electrophysical monitoring means connected to said perfusate circulating means and positioned and arranged so as to monitor electrophysical characteristics of the organ and the perfusate, to define a given quantity for the electrophysical characteristics and to generate and deliver electrical stimulation to the organ, to the perfusate or to both when the monitored electrophysical characteristics vary from within predefined limits, the electrophysical characteristics comprising a difference in charge distribution between various portions of the organ, extraneous electromagnetic stimuli, and electrical properties of the perfusate selected from the group consisting of perfusate voltage, conductance, impedance and resistance.

2. The apparatus of claim 1 wherein said electrochemical monitoring means comprises means which defines a desired pH range for the perfusate and which is electrically coupled to said electrochemical monitoring means for regulating the pH of the perfusate when the pH falls outside of the defined range.

3. The apparatus of claim 1 wherein the organ being stored is a limb and said apparatus further comprises electromyogram means.

4. The apparatus of claim 1 wherein the organ being stored is surface tissue and said apparatus further comprises means to measure alteration of surface tissue resistance.

5. The apparatus of claim 1, wherein said chamber means is further constructed so as to receive a sufficient amount of perfusate to substantially cover the organ.

6. The apparatus of claim 1 further including a self-regulating valve means positioned and arranged at at least one location at which said perfusate circulating means is supplying the perfusate to the organ to discharge perfusate to said chamber when the perfusate is being supplied to the organ at such a rate to cause an increase in pressure within the organ in excess of a predetermined pressure limit.

7. The apparatus of claim 6 wherein said temperature regulating means includes a plurality of temperature measuring probes located for measuring the temperature inside and outside the organ, and of the perfusate entering the organ, inside the organ and outside the organ.

8. The apparatus of claim 1 wherein the organ being stored is a heart and wherein said apparatus further includes a means for measuring contraction rate of the heart, and an artificial electrical stimulating means which defines a set heart contraction rate and which communicates with said contraction measuring means for receiving the measured contraction rate and for generating an electrical current which is directed through the heart when the measured contraction rate is lower than the set heart contraction rate.

9. The apparatus of claim 8 wherein said apparatus further includes a means for monitoring the onset of ventricular fibrillation of the heart and a means which is operated when the ventricular fibrillation is detected for generating and delivering to the heart an electrical countershock to the heart.

10. The apparatus of claim 9 wherein said electrophysical monitoring means comprises means for monitoring a difference in charge distribution between various portions of the organ including at least a first electrical probe positioned in the organ and at least a second electrical probe positioned external of the organ and a means for comparing the electrical charge measured by said first and second probes.

11. An apparatus for maintaining viability of animal organs for a period of time sufficient to enable the use of such organs for transplantation and medical research, said apparatus comprising:

chamber means for receiving and supporting the organ and a sufficient amount of a suitable perfusate to substantially cover the organ;

perfusate circulating means coupled to said chamber means and positioned and arranged so as to regulate supply of perfusate to the organ and to said chamber means and to collect perfusate from the organ and said chamber means;

self-regulating valve means positioned and arranged at at least one location at which said perfusate circulating means is supplying the perfusate to the organ to discharge perfusate to said chamber means when the perfusate is being supplied to the organ at such a rate to cause an increase in pressure within the organ in excess of a predetermined pressure limit;

temperature regulating means connected to said perfusate circulating means and to said chamber means and positioned and arranged so as to maintain the temperatures of the organ and the perfusate within predetermined ranges;

oxygenator means connected to said perfusate circulating means for maintaining an oxygen level in the perfusate supplied to the organ by said perfusate circulating means within a predetermined range;

electrochemical monitoring means connected to said perfusate circulating means for monitoring electrochemical characteristics of the organ and the perfusate and for maintaining the monitored electrochemical characteristics within predetermined ranges, the electrochemical characteristics comprising the ratio of intracellular to extracellular concentration of potassium ions, the extracellular concentration of sodium ions, and the pH of the perfusate; and electrophysical monitoring means connected to said perfusate circulating means and positioned and arranged so as to monitor the electrophysical characteristics of the organ and the perfusate, to define a given quantity for the electrophysical characteristics and to generate and deliver electrical stimulation to the organ, to the perfusate or to both when the monitored electrophysical characteristics vary from within predefined limits, the electrophysical characteristics comprising a difference in charge distribution between various portions of the organ, extraneous electromagnetic stimuli, and electrical properties of the perfusate selected from the group consisting of perfusate voltage, conductance, impedance and resistance.

12. The apparatus of claim 10, wherein said electrochemical monitoring means comprises means which defines a desired pH range for the perfusate and which is electrically coupled to said electrochemical monitoring means for regulating the pH of the perfusate when the pH falls outside of the defined range.

13. The apparatus of claim 11, wherein said means for monitoring a difference in charge distribution between various portions of the organ includes at least a first probe positioned in the organ and at least a second probe positioned external of the organ and a means for comparing the electrical charge measured by said first and second probes.

14. The apparatus of claim 11 wherein said self-regulating valve means comprises:

a body in which is defined first and second passageways which are separated by a partition which defines an opening smaller than at least said first passageway, said second passageway being coupled to the organ at said at least one location and to said perfusate circulating means to allow the perfusate to flow therethrough into the organ;

a member mounted for reciprocal movement in said first passageway, said reciprocal member cooperating with said partition when in contact therewith to prevent the flow of any perfusate into said first passageway from said second passageway; and resilient means which acts upon said reciprocal member to maintain said member in contact with said partition until a predefined fluid pressure is reached in said second passageway by the flow of the perfusate into said second passageway from said perfusate circulating means, whereby said member becomes dislodged from said partition to allow the perfusate to flow from said second passageway to said first passageway.

15. The apparatus of claim 14 wherein said self-regulating valve means first passageway further includes ports through which the perfusate entering said first passageway from said second passageway can exit said valve body when said member is dislodged from said partition.

16. The apparatus of claim 15 wherein said self-regulating valve means further includes a means for measuring the fluid pressure in said second passageway.

17. The apparatus of claim 11 wherein the organ being stored is a heart and wherein said apparatus further includes a means for measuring contraction rate of the heart, and an artificial electrical stimulating means which defines a set heart contraction rate and which communicates with said contraction measuring means for receiving the measured contraction rate and for generating an electrical current which is directed through the heart when the measured contraction rate is lower or higher than the set heart contraction rate.

18. The apparatus of claim 17 wherein said apparatus further includes a means for monitoring the onset of ventricular fibrillation of the heart and a means which is operated when the ventricular fibrillation is detected for generating and delivering to the heart an electrical countershock to the heart.

19. The apparatus of claim 18 wherein said temperature regulating means includes a plurality of temperature measuring probes located for measuring the temperature inside and outside the organ, and of the perfusate entering the organ, inside the organ and outside the organ.

20. The apparatus of claim 19 wherein said temperature regulating means maintains the temperature in a range of from about 15° C. to about 27° C.

21. A method for maintaining the viability of animal organs which are supported in a chamber for a period of time sufficient to enable the use of such organs for transplantation and medical research, said method comprising the steps of:

circulating a perfusate through the organ and said chamber;

regulating the perfusate temperature flowing through the organ and said chamber to maintain the perfusate and the organ within desired temperature ranges;

oxygenating the perfusate prior to circulating the perfusate through the organ and said chamber;

monitoring electrochemical characteristics of the organ and the perfusate and maintaining the electrochemical characteristics within predetermined ranges, the electrochemical characteristics comprising the ratio of intracellular to extracellular concentration of potassium ions, the extracellular concentration of sodium ions, and the pH of the perfusate; monitoring electrophysical characteristics of the organ and the perfusate, the electrophysical characteristics comprising a difference in charge distribution between various portions of the organ, extraneous electromagnetic stimuli, and electrical properties of the perfusate selected from the group consisting of perfusate voltage, conductance, impedance and resistance; and generating and delivering electrical stimulation to the organ, to the perfusate or to both when the measured electrophysical characteristics vary from within predefined limits.

22. The method of claim 21 further including the steps of:

defining a quantity for at least one of the electrophysical characteristics;

analyzing the monitored electrophysical characteristics of the organ and the perfusate to determine a quantity for each of the characteristics; and stimulating the organ when the monitored electrophysical characteristics of the organ and the perfusate vary from the defined quantity for the at least one electrophysical characteristic.

23. The method of claim 22 further including the step of:

managing the amount of the perfusate being circulated through the organ to ensure that when the pressure in the organ developed by the circulating perfusate exceeds a prescribed quantity that a sufficient amount of the perfusate is diverted from entering the organ.

24. The method of claim 23 wherein said monitoring of the difference in charge distribution between various portions of the organ includes;

positioning at least a first electrical probe in the organ and at least a second electrical probe externally of the organ; and comparing the electrical charge measured by said first and second probes.

* * * * *

UNITED STATES PATENT AND TRADEMARK OFFICE
CERTIFICATE OF CORRECTION

PATENT NO. : 5,051,352

DATED : Sep. 24, 1991

INVENTOR(S) : Martindale et al.

It is certified that error appears in the above-identified patent and that said Letters Patent is hereby corrected as shown below:

Col. 14, line 48 change "!0" to "10"

Signed and Sealed this

Second Day of March, 1993

*Attest:*

STEPHEN G. KUNIN

*Attesting Officer*     Acting Commissioner of Patents and Trademarks